United States Patent [19]
Thornton

[11] Patent Number: 5,573,509
[45] Date of Patent: Nov. 12, 1996

[54] CATHETER WITH AN EXPANDABLE PERFUSION SLIT

[75] Inventor: Troy L. Thornton, San Francisco, Calif.

[73] Assignee: Advanced Cardiovascular Systems, Inc., Santa Clara, Calif.

[21] Appl. No.: 343,183

[22] Filed: Nov. 22, 1994

[51] Int. Cl.⁶ ................................................. A61M 29/00
[52] U.S. Cl. ........................... 604/102; 604/96; 604/280
[58] Field of Search ........................... 604/96, 101, 102, 604/104, 105–109, 280; 606/192, 194, 198

[56] References Cited

U.S. PATENT DOCUMENTS

| | | | |
|---|---|---|---|
| 5,224,938 | 7/1993 | Fenton, Jr. ........................... | 604/247 |
| 5,306,250 | 4/1994 | March et al. ........................... | 604/104 |
| 5,378,237 | 1/1995 | Boussignac et al. ........................... | 604/96 |

*Primary Examiner*—Corrine M. McDermott
*Attorney, Agent, or Firm*—Heller, Ehrman, White & McAuliffe

[57] ABSTRACT

An intravascular catheter such as a dilatation catheter for angioplasty procedures which is provided with a perfusion lumen and having one or more expandable proximal perfusion openings such as closed ended slits which are expanded when the body lumen is occluded so as to facilitate the perfusion of body fluid such as oxygenated blood into the perfusion lumen. An expandable member is disposed within the perfusion lumen to expand the perfusion openings.

14 Claims, 4 Drawing Sheets

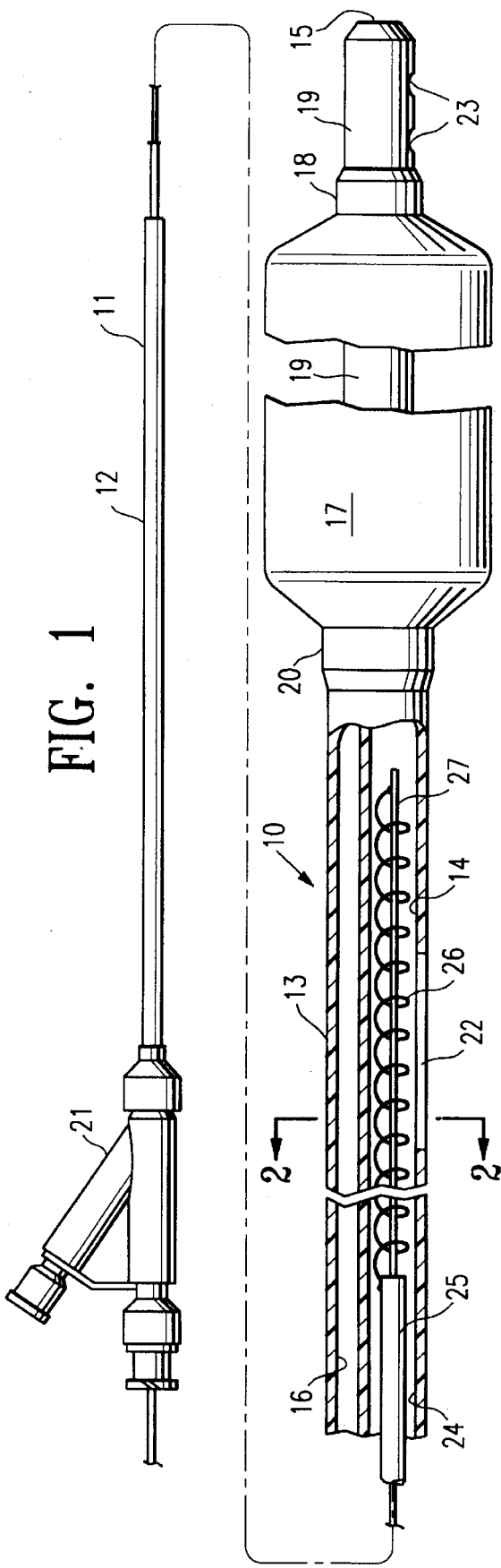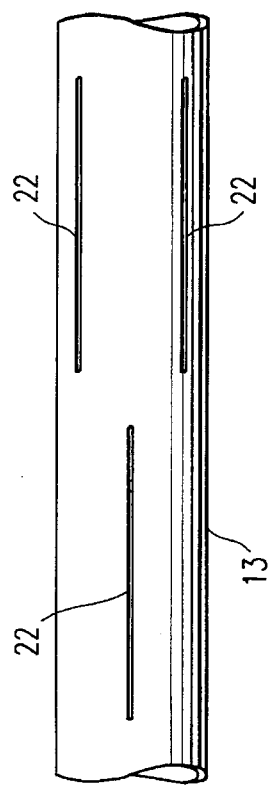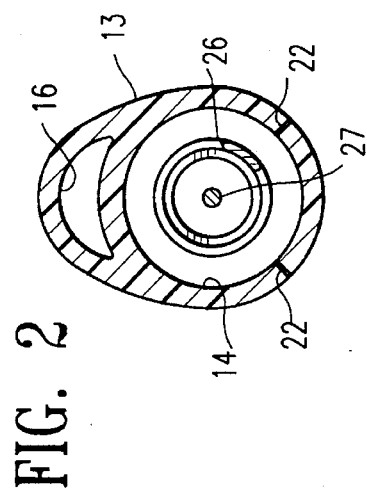

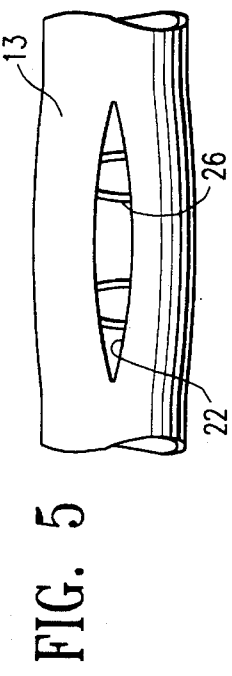
FIG. 5
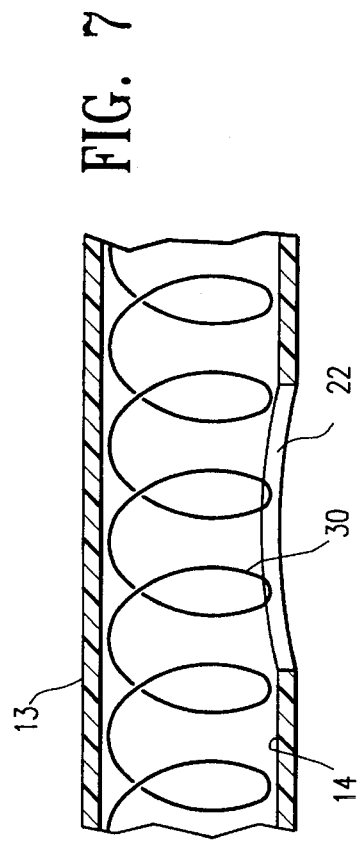
FIG. 7
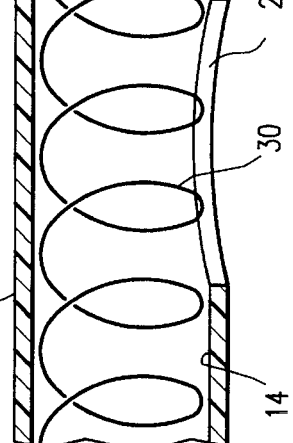
FIG. 4
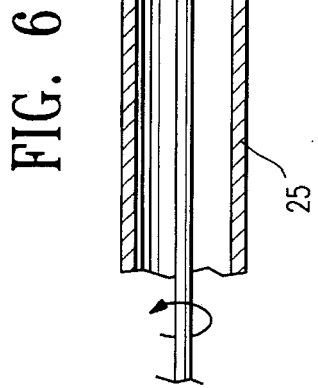
FIG. 6
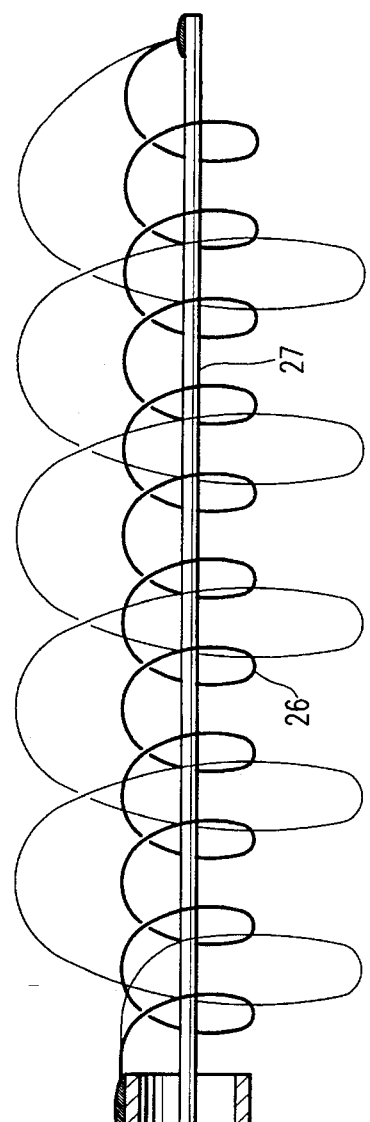

CATHETER WITH AN EXPANDABLE PERFUSION SLIT

BACKGROUND OF THE INVENTION

This invention generally relates to the field of intravascular catheters, and more particularly to a dilatation catheter for percutaneous transluminal coronary angioplasty (PTCA) having perfusion capabilities.

PTCA is now one of the most widely used treatment modalities for heart disease. The procedure basically comprises advancing a dilatation catheter, having an inflatable dilatation balloon on the distal portion thereof, into the patient's coronary anatomy until the balloon is properly positioned across the lesion to be dilated. Once properly positioned, the dilatation balloon is inflated with liquid to a predetermined size at relatively high pressures to expand the arterial passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter can be removed therefrom.

Long term dilatation has many clinical advantages, including the elimination of sudden occlusion of an arterial passageway due to an arterial dissection. However, in order to effect long term dilatation some provision must be made to perfuse oxygenated blood distal to the catheter during the long term dilatation. One perfusion-type dilatation catheter which has met with a great deal of commercial success is the RX® Perfusion Dilatation Catheter which is available from the assignee of the present invention Advanced Cardiovascular Systems, Inc. The latter catheter has recently been replaced by a perfusion dilatation catheter sold by the present assignee under the trademark FlowTrack. These perfusion catheters have a plurality of perfusion ports in the wall forming at least part of the catheter body proximal to the balloon which are in fluid communication with a guidewire receiving inner lumen extending to the distal end of the catheter body. A plurality of perfusion ports are also preferably provided in the catheter body distal to the balloon which are also in fluid communication with the inner lumen extending to the distal end of the catheter body. When the balloon on the distal extremity of the dilatation catheter is inflated to dilate a stenosis, oxygenated blood in the artery or the aorta or both, depending upon the location of the dilatation catheter within the coronary anatomy, is forced to pass through the proximal perfusion ports, through the inner lumen of the catheter body and out the distal perfusion ports. This provides oxygenated blood downstream from the balloon while it is inflated to thereby prevent or minimize ischemic conditions in tissue distal to the catheter. The balloon can be inflated for long term dilatations with essentially no damage to tissue distal to the catheter. As is appreciated by those skilled in the art, tissue distal to a stenosis is frequently already in jeopardy due to ischemic conditions which may exist from the stenotic blockage. As a result, care should be exercised in sizing the perfusion ports and the inner lumen to ensure that there is adequate flow of oxygenated blood to tissue distal to the catheter. Providing larger perfusion ports can increase the blood flow but with larger perfusion ports there is a greater chance that a guidewire passing through the perfusion lumen can pass through a perfusion port. Providing a greater number of small perfusion ports increases the resistance to flow reducing the amount of blood which can flow through the catheter.

What has been needed is a perfusion type dilatation catheter which has one or more perfusion openings which can facilitate greater blood flow but which prevents guidewire excursions through the perfusion ports.

SUMMARY OF THE INVENTION

The present invention is directed to an intravascular catheter, such as a dilatation catheter for angioplasty procedures, which has an opening in the catheter shaft which can be expanded to facilitate flow of body fluid therethrough, such as oxygenated blood, when the body lumen in which the catheter is disposed is occluded.

The intravascular catheter of the invention generally has an elongated catheter shaft with proximal and distal ends, a port or opening in the distal end, one or more expandable perfusion openings in a distal portion of the catheter shaft and a perfusion lumen extending within the distal portion of the catheter shaft from one or more of the expandable perfusion opening to the, port in the distal end. Means are provided to expand the perfusion lumen at least adjacent the perfusion openings to expand these openings to facilitate the flow of body fluid through the perfusion openings into the perfusion lumen and out the one or more of distal perfusion openings or ports provided in the distal portion of the shaft distal to the expandable perfusion openings.

Generally, the perfusion openings are elongate with the transverse dimension of the opening in the unexpanded condition smaller than the diameter of the distal tip of the guidewire used to prevent the distal tip of the guidewire from exiting through a perfusion opening. In a presently preferred embodiment, the expandable perfusion openings are slits which are closed at both ends, i.e. they do not continue to an opening such as a guidewire port, to prevent guidewire excursions therethrough.

A presently preferred embodiment of the invention is a perfusion type dilatation catheter which has an elongated catheter shaft with proximal and distal ends, an inflation lumen extending within the catheter shaft to a location on a distal section of the shaft spaced proximal to the distal end, a dilatation balloon on the distal section having an interior in fluid communication with the inflation lumen and an adapter on the proximal end of the catheter shaft. A guidewire receiving perfusion lumen extends within the catheter shaft at least within the distal shaft section from a location proximal to the dilatation balloon to the port in the distal end of the catheter shaft. The catheter shaft has at least one expandable, closed ended perfusion slit in the catheter shaft proximal to the dilatation balloon which is in fluid communication with the guidewire receiving perfusion lumen. One or more perfusion ports or slits may also be provided on the shaft distal to the dilatation balloon. In accordance with the invention, means are provided within the guidewire receiving perfusion lumen to expand the interior of the perfusion lumen adjacent to the perfusion slit to open up the slit and facilitate the flow of oxygenated blood through the expanded opening into the perfusion lumen to facilitate blood flow when the inflated dilatation balloon occludes the arterial passageway. A plurality of slits are provided in the catheter shaft adjacent to the proximal end of the balloon skirt for maximum flow.

A variety of suitable means to expand the perfusion lumen in order to open up the perfusion lumen are contemplated and will be readily apparent to those skilled in the art. One expandable means devised is an elongated torqueable tubular member with a helical coil secured by its proximal end to the distal end of the tubular member and extending distal to the tubular member. An operating shaft extends through the torqueable tubular member and the coil and is secured by its distal end to the distal end of the coil. The expandable means is advanced through the perfusion lumen until the coil is at a desired location therein and then relative rotation is effected between the operating shaft and the tubular member to expand the helical coil which in turn expands the perfusion lumen of the catheter, opening the perfusion opening. Upon completion of the dilatation and deflation of the balloon, relative rotation may then be effected between the tubular member and the operating shaft in a direction opposite to the first rotation to contract the helical coil to facilitate its removal.

Another expandable means, similar to the first means, has a high strength tubular member with an expandable cage of braided high strength strands such as wires which is secured to the distal end of the tubular member. A control line extends through an inner lumen of the high strength tubular member and the interior of the expandable cage and is secured to the distal end of the expandable cage. Movement of the ends of the cage toward one another increases the cage's diameter, which in turn is utilized to expand the perfusion lumen to open the perfusion slit and allow blood flow through the perfusion lumen when the dilatation balloon is inflated. Upon deflation of the balloon, the ends of the cage may then be moved apart to reduce the diameter of the cage to facilitate the removal of the expandable means.

Another means for expansion of the perfusion lumen includes an expandable member similar to a stent, such as an elongated helical coil, disposed within the perfusion lumen and is formed of a shape memory alloy adapted to expand upon reaching a temperature at body temperature or a temperature above body temperature which does not damage tissue within the arterial passageway. The expanded coil opens the perfusion slit as in the previous embodiments. Another means includes a self expandable member such as a cage which is covered with a sheath to prevent expansion while being advanced within a body lumen, but which expands when the sheath is removed.

The expandable perfusion slit simplifies the manufacture of the catheter and provides improved perfusion flow while preventing guidewire excursions through the perfusion openings. These and other advantages of the invention will become more apparent from the following detailed description thereof when taken in conjunction with the accompanying exemplary drawings.

BRIEF DESCRIPTION OF THE DRAWINGS

FIG. 1 is an elevational view, partially in section, of a perfusion dilatation catheter embodying features of the invention.

FIG. 2 is a transverse cross-sectional view of the catheter shown in FIG. 1 taken along the lines 2—2.

FIG. 3 is a bottom view of the distal section of the catheter shown in FIG. 1.

FIG. 4 is a transverse cross-sectional view of the catheter as shown in FIG. 2 with the perfusion slit in an opened condition.

FIG. 5 is a bottom view of the distal section of the catheter as shown in FIG. 3 with the perfusion slit in an opened condition.

FIG. 6 is a longitudinal view, partially in section, of the expanding means shown in FIGS. 1–3.

FIG. 7 is a partial longitudinal cross-sectional view of an alternative embodiment of the invention wherein the expanding means is a coil formed of a shape memory alloy which expands at or above body temperature.

DETAILED DESCRIPTION OF THE INVENTION

Figure 8:
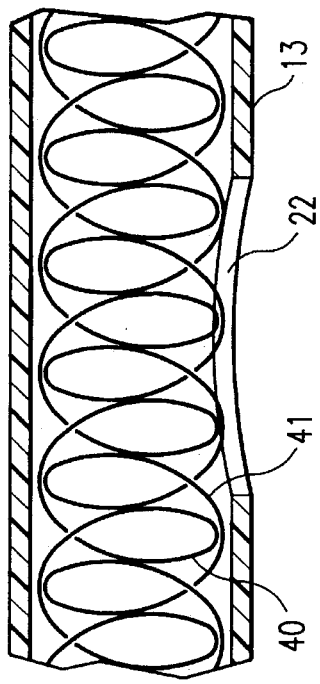
FIG. 8 is a partial longitudinal cross-section of an alternative embodiment of the invention wherein the expanding means is a pair of helical coils formed of a shape memory alloy which are oppositely wrapped.

FIGS. 1–3 schematically illustrate an over-the-wire, perfusion-type dilatation catheter 10 embodying features of the invention. The catheter 10 generally includes an elongated catheter shaft 11 which has a proximal section 12 and a distal section 13, a guidewire receiving perfusion lumen 14 which extends to a guidewire port 15 in the distal end of the catheter shaft and an inflation lumen 16 which extends through the catheter body to a location spaced proximally from the distal end of the catheter shaft. A inflatable dilatation balloon 17 is mounted on the distal section 13 of the catheter shaft 11 with the distal end or skirt 18 of the balloon being secured in a suitable manner to the distal extremity of a tubular extension 19 of the catheter shaft 11 which extends through the interior of the balloon and the proximal end or skirt 20 of the balloon being secured in a suitable manner to the distal end of the tubular extension 19. A multiarm adapter 21 is secured to the proximal end of the shaft.

The distal shaft section 13 has a plurability of proximal perfusion slits 22 which pass through the wall of the catheter shaft 11 partially defining the guidewire receiving perfusion lumen 14 and which are in fluid communication with the perfusion lumen. The perfusion slits 22 are closed at both ends i.e. they do not extend to an opening such as a guidewire port. A plurality of distal perfusion ports 23 are provided in the portion of the tubular extension 19 which extends out the distal end of the balloon 17. Perfusion slits such as slits 22 may be employed instead of ports as shown.

An expanding assembly 24 is disposed within the guidewire receiving perfusion lumen 14 which comprises an elongated torqueable tubular member 25, a helical coil 26 secured to the distal end of the tubular member at its proximal end and an elongated operating shaft 27 which extends through the interior of the tubular member and the helical coil and is secured to the distal end of the coil. Relative rotation between the torqueable tubular member 25 and the operating shaft 27 causes the expansion and contraction of the coil 26. The expansion of the coil 26 is illustrated in FIGS. 4 and 5 with the resulting opening or expansion of the proximal perfusion slits 22. An enlarged view of the expanding member 24 is given in FIG. 6 with the expansion of the coil 26 being shown in phantom. The individual turns of the coil 26 may be stacked adjacent to one another or spaced from each other in the contracted state. The operating shaft 27 may be moved longitudinally to elastically stretch the coil 26 and to decrease the diametrical dimension of the coil.

The catheter 10 may be advanced over a guidewire into the patient's coronary artery in a conventional manner as previously described in the BACKGROUND OF THE INVENTION until the balloon 17 is located in a desired position within the patient's coronary artery where the dilatation is to occur. Once in position, the guidewire may be removed and the expanding assembly 24 may then be advanced through the perfusion lumen 14 until the expandable coil 26 is disposed within the perfusion lumen from the most proximal perfusion slit 22 to the most distal perfusion port 23. Rotation of the operating shaft 26 expands the coil 25 which in turn expands the perfusion lumen 14 and the perfusion slits 21 as shown in FIGS. 4 and 5. The operating shaft 27 may be manually held in the rotated position or a suitable means may be provided to maintain the rotated position with respect to the high strength tubular member 25. The balloon 17 may then be inflated for purposes of dilating the stenotic region of the patient's coronary arteries. When the balloon 17 is inflated during an angioplasty procedure, oxygenated blood is forced to pass through the opened proximal perfusion slits 22, through the perfusion lumen 14 and then out the distal perfusion ports 23 to provide oxygenated blood distal to the catheter 10 and to thereby avoid the generation of or the exacerbation of ischemic conditions in tissue downstream thereof. The high strength tubular member 25 of the expanding assembly 24 is preferably withdrawn sufficiently within the perfusion lumen 14 before the coil 26 is expanded so as to avoid impeding blood flow through the perfusion lumen 14. With the expanded perfusion lumen, long term dilatations may be employed.

The dimensions of the dilatation catheter generally follows the dimensions of commercially available dilatation catheters. The overall length may range from about 120 to about 175 cm, typically about 135 cm, the outer diameter of the catheter shaft about 0.03 to about 0.07 inch (0.76–1.78 mm). The diameter of the guidewire receiving perfusion lumen in the unexpanded state is about 0.01 to about 0.02 inch (0.25–0.51 mm) and in the expanded state is typically about 0.01 to about 0.02 inch (0.25–0.051 mm) larger than the unexpanded state. Greater or lesser expansion may be utilized depending upon the dimensions needed for adequate flow.

The overall length of the expanding assembly is approximately the same as the dilatation catheter and preferably is slightly longer, e.g. about 135 to about 195 cm, typically about 150 cm. The high strength tubular member 25 is about 90 to about 120 cm in length and about 0.015 to about 0.026 inch (0.38–0.66 mm) in outer diameter. The wall thickness ranges from about 0.001 to about 0.003 inch (0.025–0.076 mm) if the tubular member is formed of stainless steel, but other wall thicknesses may be utilized with materials of different tensile strengths. The coil 26 should be long enough to expand at least a significant length of the perfusion lumen 14 and is preferably long enough to extend from a location proximal to the proximal perfusion slits to a location distal thereto, e.g. about 10 to about 40 cm in length. The outer diameter of the coil 26 in the unexpanded condition should be about 0.01 to about 0.02 inch the outer diameter of the high strength tubular member 25. The transverse dimensions of the wire forming the coil 26 will vary depending upon the forces needed to expand the walls defining the perfusion lumen 14 and may have a circular or rectangular transverse cross-sectional shape. If formed of conventional 304 stainless steel, the diameter of the wire should be about 0.001 to about 0.003 inch (0.025–0.076 mm). It may also be formed of superelastic NiTi alloy. The operating shaft 27 is longer, e.g. about 10 to about 20 cm longer, than the combined lengths of the high strength tubular member 25 and the coil 26 and may be formed of conventional 304 stainless steel wire about 0.006 to about 0.012 inch (0.15–0.3 mm) in diameter. It also may be formed of a superelastic NiTi alloy. The diametrical dimensions may be varied depending upon the tensile strength of the material. For example, if the operating shaft 27 is formed of a Co—Ni—Cr—Mo type alloy, which has tensile strengths greater than 300 ksi, its diameter may be reduced considerably. Further information concerning the Co—Ni—Cr—Mo type alloys can be found in copending application Ser. No. 08/280,209, filed on Jul. 25, 1994, which is incorporated herein in its entirety by reference. A suitable commercially available alloy is the alloy designated as MP35N (Carpenter Technology Corporation) which has a nominal composition of about 35% cobalt, about 35% nickel, about 20% chromium and about 10% molybdenum.

The method of bonding the proximal and distal ends 19 and 20 of the balloon 17 may be effected in a variety of conventional ways. For example, the components may be heat or fusion bonded or bonded by a suitable adhesive such an a epoxy or cyanoacrylate adhesive. To the extent not otherwise described, the catheter and the expandable means of the invention may be formed by conventional techniques used in manufacturing intravascular catheters and guidewires.

FIG. 7 depicts an alternative embodiment of the invention wherein a coil 30 formed of shape memory alloy such as NiTi alloy with 50% (atomic) Ni and 50% (atomic) Ti is disposed within the perfusion lumen 14 of inner tubular 31 which expands at or above body temperature. The alloy formulation and the thermomechanical processing can be varied to obtain the tensile strength needed which provides adequate expansion of the perfusion lumen at the remembered expanded shape. Moreover, the alloy formulation and thermomechanical processing may also be varied to control the final transformation temperature from the martensite phase to the austenite phase, i.e. the $A_f$ temperature. The remembered shape in the austenite phase is the expanded state and the contracted state is in the martensite phase. Raising the temperature of the shape memory alloy to above the $A_f$ temperature transforms the deformed martensite phase into the remembered shape in the austenite phase. Details of the alloy formulation and the thermomechanical processing are well known to those skilled in the metallurgical arts. For a shape memory alloy with an $A_f$ temperature at body temperature the alloy must be maintained at a temperature below body temperature by suitable insulation until the catheter is in the desire position within the patient's coronary artery. Once in position and perfusion begins, the temperature of the alloy quickly rises to body temperature and the coil then expands within the perfusion lumen expanding the inner diameter thereof. For the shape memory alloy with an $A_f$ temperature above body temperature, the shape memory alloy must be heated to a temperature above body temperature to effect the expansion, Resistance or inductive heating of the coil may be employed to raise the temperature of the coil. A variety of other means may also be employed such as injecting saline at an elevated temperature above body temperature. FIG. 8 depicts a modification of the embodiment shown in FIG. 7 wherein a pair of such coils 40 and 41 are disposed within the perfusion lumen 14 to expand the lumen. More than two coils may be used if desired or needed.

Figure 9:
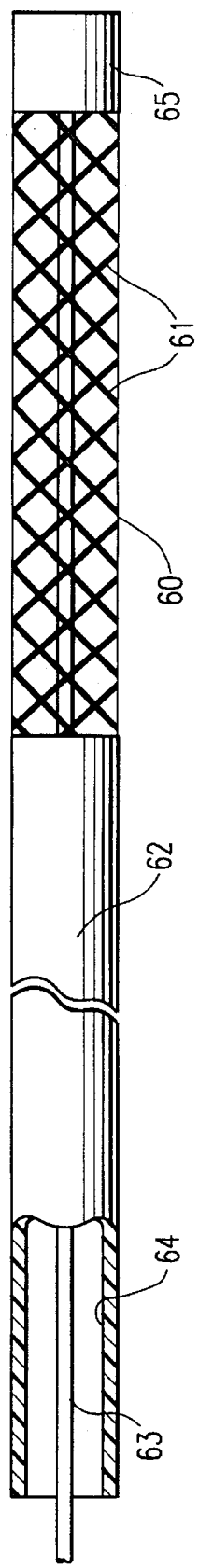
FIGS. 9 and 10 are elevational views of an alternative embodiment wherein the expanding means is a cage which is formed of interwoven high strength strands and which contracts diametrically when the cage is elongated as shown in FIG. 9 and expands diametrically when the cage is shortened as shown in FIG. 10.
Figure 10:
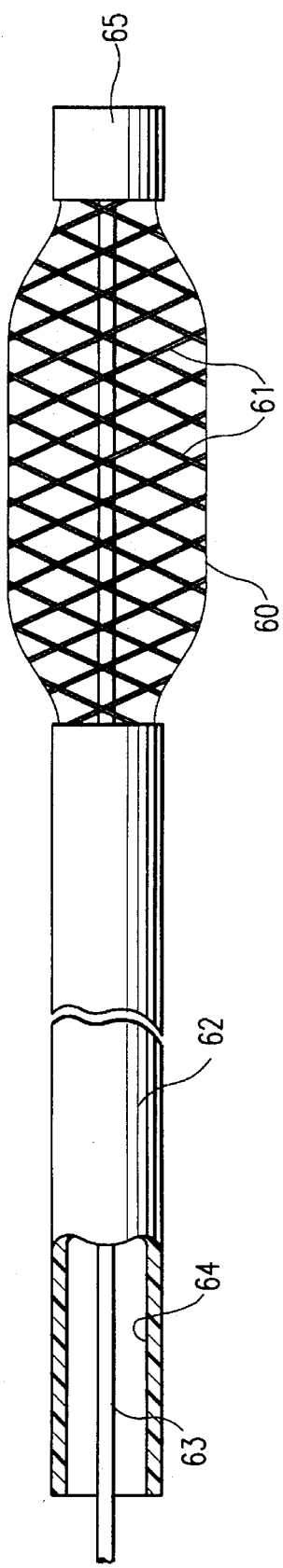

FIGS. 9 and 10 illustrate another alternative embodiment which includes an expandable cage 60 formed of high strength strands 61 such as stainless steel, Co—Ni—Cr—Mo alloys and the like and secured to the distal end of a tubular member 62. A control line 63 extends through the inner lumen 64 of the tubular member 62 and the expandable cage 60 and is secured to a collar 65 secured to the distal end of the cage 60. Applying tension to the control line 63 shortens the length of the cage 60 but in the process of shortening the cage its diameter-expands, as shown in FIG. 10. If the strands 61 of the cage 60 are in an unstressed condition when the cage is in the elongated condition and in a stressed condition when the cage is expanded, the control line will only have to apply tension to the distal end of the cage 60 to expand the cage and the relaxing of the strands forming the cage when the tension is removed can be relied upon to return the cage to its elongated condition. In this case the control line 63 may be either flexible or stiff. However, if the expanded cage needs the application of an axial force to return to the elongated condition, then the control line 63 must be stiff enough to apply the required axial force.

The tubular member of the expandable assembly may be formed of suitable high strength materials such as high strength polymeric materials such a polyamide or polyetheretherketone, stainless steel, a pseudoelastic alloy such as NiTi alloy or the Co—Ni—Cr—Mo alloy mentioned above. The control line may be made of the same or similar suitable high strength polymer or metallic materials.

Figure 12:
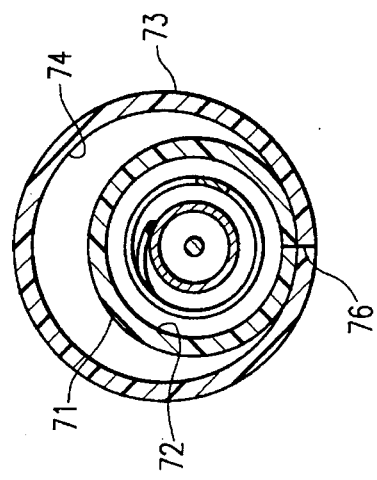
FIG. 12 is a transverse cross-sectional view of the embodiment shown in FIG. 11 taken along the lines 12—12.
Figure 11:
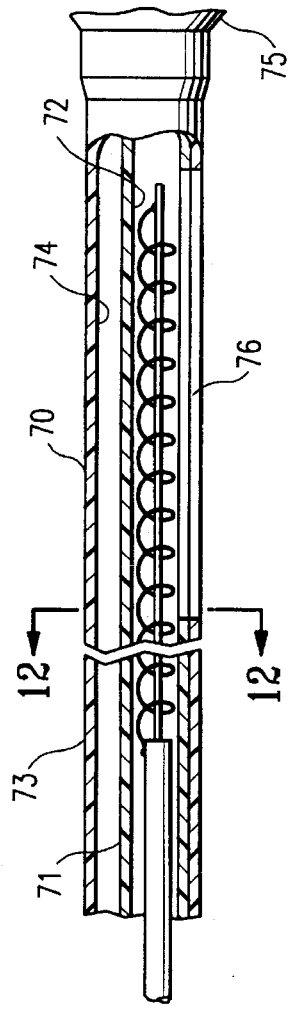
FIG. 11 is a longitudinal cross-sectional view of an alternative shaft construction having an inner and outer tubular members.

FIGS. 11 and 12 illustrate an alternative embodiment of the invention in which the catheter shaft 70 includes inner tubular member 71 with guidewire receiving perfusion lumen 72 and outer tubular member 73 disposed about the inner tubular member 71 and defining inflation lumen 74. The inner tubular member 71 is secured to the interior of the outer tubular member 73 along a length thereof in a distal portion of the catheter shaft 70 proximal to the dilatation balloon 75. One or more perfusion slits 76 are provided through the walls of the inner tubular member and the outer tubular member where they are bonded together. The slits 76 are opened up in the same manner as the previously discussed embodiments.

Figure 13:
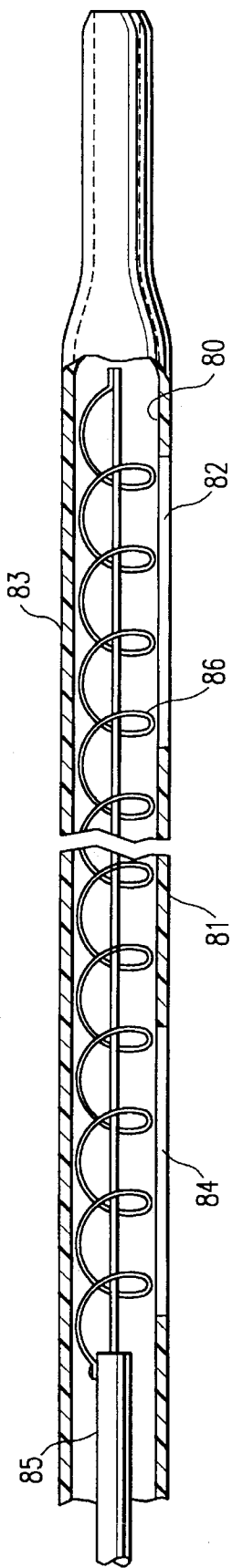
FIG. 13 is an elevational view, partially in section of a bail-out type intravascular catheter embodying features of the invention.

The present invention has been described herein in terms of dilatation catheters for angioplasty procedures. However, the invention may be utilized in a variety of intravascular catheters. For example, an expandable perfusion lumen 80 may be incorporated into a bail-out catheter 81 as shown in FIG. 13. Perfusion ports 82 are provided in the distal shaft portion 83 spaced from the distal end and one or more proximal perfusion slits 84 are provided in the distal shaft portion spaced proximally from the distal perfusion ports and proximally from the distal end of the catheter shaft. Expanding assembly 85 with expandable coil 86 is disposed within the perfusion lumen 80 to be expanded in the same manner as the expandable member shown in FIG. 4 to increase perfusion flow through the lumen 80 as in the prior embodiments. As well known by those skilled in the art of interventional cardiology, bail-out devices are employed when an interventional procedure such as angioplasty results in the sudden occlusion of a coronary artery.

In yet another method of expanding the perfusion opening, the perfusion lumen is provided with an oblong transverse shape, i.e. having a short transverse dimension and a long transverse dimension, and a mandrel having an outer diameter, if circular, or other dimension corresponding to the short transverse dimension of the perfusion lumen which is larger than the short transverse dimension of the perfusion lumen. The mandrel is advanced into the perfusion lumen causing the slit to open up. However, the mandrel must have a open structure, because, if otherwise, the perfusion openings would be blocked. A variety of other means may be employed to expand the perfusion lumen to open the perfusion opening.

Although individual features of embodiments of the invention may be shown in some of the drawings and not in others, those skilled in the art will recognize that individual features of one embodiment of the invention can be combined with any or all the features of another embodiment. While the invention is described herein in terms of certain preferred embodiments, it is apparent that various modifications and improvements may be made to the invention without departing from the scope thereof.

What is claimed is:

1. A perfusion dilatation catheter comprising:

a) an elongated catheter shaft having proximal and distal ends, a port in the distal end, proximal and distal shaft sections, an inflation lumen extending within the proximal shaft section and the distal shaft section to a discharge location in the distal shaft section spaced proximally from the distal end of the catheter shaft having a discharge port therein, a perfusion lumen extending at least within the distal shaft section to the port in the distal end of the catheter shaft and at least one elongated perfusion opening in the catheter shaft which has closed proximal and distal ends and which is in fluid communication with the perfusion lumen;

b) an inflatable dilatation member having an elongated cylindrically shaped working section and tapered proximal and distal ends which is disposed on the distal shaft section distal to the elongated perfusion opening in the catheter shaft having an interior in fluid communication with the inflation lumen at the discharge location; and c) means to increase at least one transverse dimension of the perfusion lumen underlying the elongated perfusion opening in the catheter shaft to open the elongated perfusion opening between the closed ends thereof to facilitate the flow of blood therethrough into the perfusion lumen, through the perfusion lumen to the port in the distal end of the catheter shaft when the dilatation member is inflated within a patient's artery.

2. The dilatation catheter of claim 1 wherein the perfusion opening is a slit.

3. The dilatation catheter of claim 1 wherein the means to increase at least one transverse dimension of the perfusion lumen under the perfusion opening includes an expandable coil having proximal and distal ends.

4. The dilatation catheter of claim 3 wherein the means to increase at least one transverse dimension of the perfusion lumen includes an elongated high strength tubular member with proximal and distal ends and an inner lumen extending therein with the expandable coil secured by its proximal end to the distal end of the high strength tubular member.

5. The dilatation catheter of claim 4 wherein the means to increase at least one transverse dimension of the perfusion lumen includes an elongated operating shaft which has proximal and distal ends, which extends within the inner lumen of the high strength tubular member and within the coil and which is secured by its distal end to the distal end of the coil.

6. The dilatation catheter of claim 5 wherein the coil is expanded by effecting relative axial rotation between the operating shaft and high strength tubular member to which the coil is secured.

7. The dilatation catheter of claim 1 wherein the means to increase at least one transverse dimension of the perfusion lumen includes an expandable tubular member formed of a shape memory alloy.

8. The dilatation catheter of claim 7 wherein the shape memory alloy has a final transformation temperature at least as high as body temperature.

9. The dilatation catheter of claim 7 wherein the shape memory alloy has a final transformation temperature which is above body temperature.

10. The dilatation catheter of claim 1 wherein the means to increase at least one transverse dimension of the perfusion lumen includes an expandable cage having proximal and distal ends and a control line having proximal and distal ends which extends within the cage with the distal end of the control line being secured to the distal end of the cage.

11. The dilatation catheter of claim 10 wherein the means to increase at least one transverse dimension of the perfusion lumen includes an elongated high strength tubular member with proximal and distal ends and an inner lumen extending therein, with the expandable cage being secured by the proximal end thereof to the distal end of the high strength tubular member and the distal end of the cage having a collar thereon, and the control line extending within the cage, and with the distal end of the control line being secured to the collar on the distal end of the cage.

12. The dilatation catheter of claim 11 wherein the cage is expanded by applying tension to the proximal end of the control line which extends out the proximal end of the high strength tubular member to which the cage is secured, the application of tension shortening the length of the cage and expanding the diameter thereof.

13. A method of performing an intravascular procedure comprising:

a) providing an intravascular catheter having a catheter shaft with proximal and distal ends, a port in the distal end of the catheter shaft, a perfusion lumen extending within a distal portion of the catheter shaft to the distal port, at least one elongated opening in the distal portion of the catheter shaft having closed proximal and distal ends and being in fluid communication with the perfusion lumen, and occluding means having a cylindrical working surface and tapered proximal and distal ends on the distal portion of the catheter shaft distal to the elongated opening:

b) advancing the catheter through the body lumen until the occluding means on the distal portion of the catheter shaft is located at a desired position within the body lumen;

c) expanding the perfusion lumen underlying the elongated opening having closed proximal and distal ends to open the opening to facilitate the flow of body fluid through the opening into the perfusion lumen, distally through the perfusion lumen and out the port in the distal end of the catheter shaft when the occlusion means occludes the body lumen; and d) expanding the occlusion means to occlude the body lumen.

14. A method of performing an angioplasty procedure comprising:

a) providing a dilatation catheter having a catheter shaft with proximal and distal ends, a port in the distal end of the catheter shaft, a perfusion lumen extending within a distal portion of the catheter shaft to the distal port, at least one elongated perfusion opening in the distal portion of the catheter shaft having closed proximal and distal ends and being in fluid communication with the perfusion lumen, and balloon dilatation means, which has a cylindrical working section and tapered proximal and distal ends, on the distal portion of the catheter shaft distal to the elongated perfusion opening;

b) advancing the catheter through a patient's vasculature until the balloon dilatation means on the distal portion of the catheter shaft is located at a stenotic arterial region within the patient's vasculature;

c) inflating the balloon dilatation means to dilate the stenotic arterial region within the patient's vasculature; and d) expanding the perfusion lumen underlying the elongated perfusion opening to expand the elongated perfusion opening to facilitate the flow of blood through the perfusion opening into the perfusion lumen, distally through the perfusion lumen and out the port in the distal end of the catheter shaft when the balloon dilatation means is inflated to dilate the stenotic region.

\* \* \* \* \*